US010292792B2

(12) United States Patent
Daftary et al.

(10) Patent No.: US 10,292,792 B2
(45) Date of Patent: May 21, 2019

(54) RESTORATION DENTAL IMPLANT AND METHOD

(71) Applicant: Nobel Biocare Services AG, Kloten (CH)

(72) Inventors: Fereidoun Daftary, Beverly Hills, CA (US); Oded Bahat, Beverly Hills, CA (US)

(73) Assignee: Nobel Biocare Services AG, Kloten (CH)

( * ) Notice: Subject to any disclaimer, the term of this patent is extended or adjusted under 35 U.S.C. 154(b) by 47 days.

(21) Appl. No.: 14/583,392

(22) Filed: Dec. 26, 2014

(65) Prior Publication Data

US 2016/0058529 A1   Mar. 3, 2016

Related U.S. Application Data

(60) Provisional application No. 62/043,777, filed on Aug. 29, 2014, provisional application No. 62/085,514, filed on Nov. 29, 2014.

(51) Int. Cl.
*A61C 8/00* (2006.01)
*A61C 8/02* (2006.01)

(52) U.S. Cl.
CPC .......... *A61C 8/0037* (2013.01); *A61C 8/0006* (2013.01); *A61C 8/0018* (2013.01); *A61C 8/0022* (2013.01); *A61C 8/0025* (2013.01); *A61C 8/0054* (2013.01); *A61C 8/0066* (2013.01); *A61C 8/0068* (2013.01); *A61C 8/0069* (2013.01); *A61C 8/0077* (2013.01); *A61C 8/0089* (2013.01)

(58) Field of Classification Search
CPC ... A61C 8/0037; A61C 8/0077; A61C 8/0025; A61C 8/0018
See application file for complete search history.

(56) References Cited

U.S. PATENT DOCUMENTS

| | | | |
|---|---|---|---|
| 4,468,200 A * | 8/1984 | Munch | A61C 8/0022 433/174 |
| D356,869 S | 3/1995 | Holmen et al. | |
| D362,720 S | 9/1995 | Holmen et al. | |
| 5,639,237 A | 6/1997 | Fontenot | |
| 5,674,069 A | 10/1997 | Osorio et al. | |
| 5,759,034 A | 6/1998 | Daftary | |
| 5,779,480 A | 7/1998 | Groll et al. | |

(Continued)

FOREIGN PATENT DOCUMENTS

| | | |
|---|---|---|
| KR | 10-0666245 B1 | 1/2007 |
| WO | WO 2006/138352 A2 | 12/2006 |

(Continued)

OTHER PUBLICATIONS

Aug. 17, 2018, International Search Report for PCT Application No. PCT/US2018/028820 filed on Apr. 23, 2018.

(Continued)

*Primary Examiner* — Jonathan Miles
*Assistant Examiner* — Stephen Sparks
(74) *Attorney, Agent, or Firm* — Knobbe, Martens, Olson & Bear LLP

(57) ABSTRACT

An implant fixture is disclosed. The implant fixture contains an elongated shaft section, and a head section, wherein the head section contains at least one concave area for bone growth therein.

4 Claims, 11 Drawing Sheets

(56) References Cited

U.S. PATENT DOCUMENTS

| | | |
|---|---|---|
| 5,785,525 A | 7/1998 | Weissman |
| 6,024,567 A | 2/2000 | Callan et al. |
| 6,039,568 A | 3/2000 | Hinds |
| D477,667 S | 7/2003 | Whitehead et al. |
| D477,876 S | 7/2003 | Whitehead et al. |
| D477,877 S | 7/2003 | Whitehead et al. |
| D477,878 S | 7/2003 | Whitehead et al. |
| D486,914 S | 2/2004 | Schulter et al. |
| D493,535 S | 7/2004 | Whitehead et al. |
| 6,854,972 B1 | 2/2005 | Elian |
| D507,052 S | 7/2005 | Wohrle et al. |
| D511,833 S | 11/2005 | Wohrle et al. |
| D528,210 S | 9/2006 | Boettcher et al. |
| 7,179,088 B2 | 2/2007 | Schulter |
| 7,249,949 B2 | 7/2007 | Carter et al. |
| 7,293,991 B1 | 11/2007 | Karapetyan |
| 7,341,453 B2 | 3/2008 | Coatoam |
| D567,947 S | 4/2008 | Lerner et al. |
| D580,059 S | 11/2008 | Boettcher et al. |
| D587,372 S | 2/2009 | Purga et al. |
| D611,603 S | 3/2010 | Noguchi et al. |
| D611,604 S | 3/2010 | Aoyagi et al. |
| D611,097 S | 5/2010 | Johnson et al. |
| D616,097 S | 5/2010 | Johnson et al. |
| D641,877 S | 7/2011 | Aldecoa et al. |
| D641,878 S | 7/2011 | Aldecoa et al. |
| D652,929 S | 1/2012 | Sibhatu et al. |
| D663,032 S | 7/2012 | Mashio et al. |
| D663,419 S | 7/2012 | Mashio et al. |
| 8,221,119 B1 | 7/2012 | Valen |
| D667,955 S | 9/2012 | Spahn et al. |
| 8,430,668 B2* | 4/2013 | Bassett ................ A61C 8/0001 433/173 |
| 8,449,297 B2 | 5/2013 | Boehm-Van Diggelen |
| 8,616,881 B2* | 12/2013 | Cottrell ................ A61C 8/0025 433/173 |
| 8,657,602 B2* | 2/2014 | Han ...................... A61C 8/0022 433/173 |
| 8,814,568 B2 | 8/2014 | Abboud |
| 8,827,704 B2* | 9/2014 | Sanders ................ A61C 1/084 433/174 |
| 9,125,710 B2 | 9/2015 | Bassett et al. |
| D765,250 S | 8/2016 | Dafarty et al. |
| D765,859 S | 9/2016 | Dafarty et al. |
| D765,860 S | 9/2016 | Dafarty et al. |
| 9,498,305 B2* | 11/2016 | Babiner ............... A61C 8/0069 |
| 9,883,925 B2 | 2/2018 | Daftary |
| 2004/0185419 A1* | 9/2004 | Schulter ............... A61C 8/0018 433/173 |
| 2007/0037122 A1 | 2/2007 | Bassett |
| 2007/0072149 A1 | 3/2007 | Rompen et al. |
| 2009/0280454 A1 | 11/2009 | Hanna |
| 2014/0106305 A1* | 4/2014 | Jacoby ................ A61C 8/0006 433/174 |
| 2014/0242546 A1 | 8/2014 | Babiner |
| 2015/0182312 A1 | 7/2015 | Hanlsch |
| 2016/0235503 A1 | 8/2016 | Haydar |
| 2017/0049539 A1 | 2/2017 | Jacoby |

FOREIGN PATENT DOCUMENTS

| | | |
|---|---|---|
| WO | WO 2008/138644 A1 | 11/2008 |
| WO | WO 2016/145394 A1 | 9/2016 |

OTHER PUBLICATIONS

Mar. 12, 2018, European Search Report for European Application No. EP 15 83 5430.
Apr. 29, 2015, International Search Report for PCT Application No. PCT/US20015/010217 filed on Jan. 6, 2015.

* cited by examiner

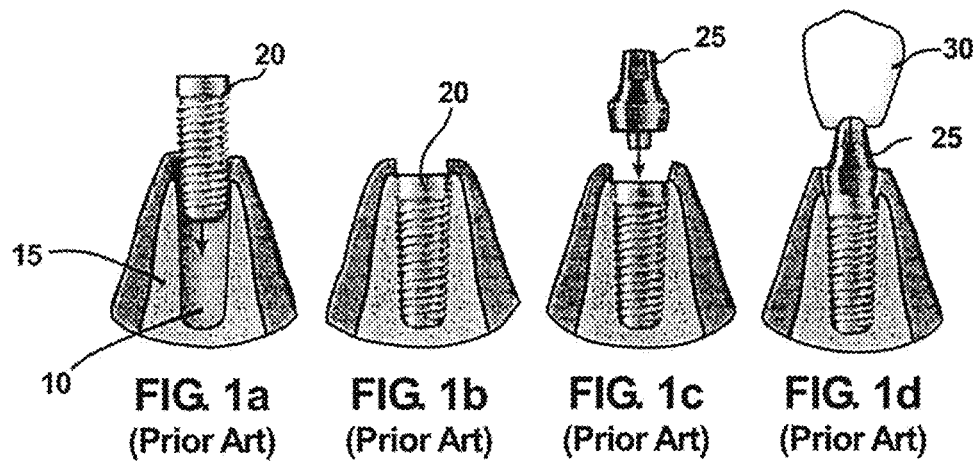

RESTORATION DENTAL IMPLANT AND METHOD

CROSS REFERENCE TO RELATED APPLICATIONS

This application claims the benefit of U.S. Provisional Application No. 62/043,777, filed on Aug. 29, 2014, which is incorporated herein by reference in its entirety. This application claims the benefit of U.S. Provisional Application No. 62/085,514, filed on Nov. 29, 2014, which is incorporated herein by reference in its entirety.

FIELD

The present invention relates to the filed of dental implants.

BACKGROUND

Restorations supported by dental implants with adjacent and/or opposing teeth have been performed by thousands of clinicians. An exemplary restoration process is shown in FIGS. 1a-d. Referring to FIGS. 1a, an alveolus 10 is formed in a patient's jawbone 15 to accommodate a dental implant fixture 20. Once the dental implant fixture 20 is securely in the alveolus 10 (shown in FIG. 1b), an abutment member 25 is coupled with the dental implant fixture 20 (shown FIGS. 1c-d). The restoration process is completed after tooth analogue 30 is coupled with the abutment member 25.

In view of the recent research, it has been determined that some people with single-tooth and/or multiple-tooth implant restorations exhibit esthetic, functional, restorative and/or periodontal ramifications of subtle continued craniofacial growth that occurs after the implant restorations are performed.

Craniofacial growth may influence the relationship of implant restorations to the remaining teeth and jaw structure by, for example, causing changes in occlusion, causing migration of teeth with subsequent effect of opening contact, and/or causing changes to anterior esthetic.

Changes in occlusion can be due to continued growth in the arch containing the implants, as well as the opposing arch. In both situations, the position of the implants and associated restoration are static whereas the teeth are subject to movement in both facial and occlusal directions. These potential changes are not gender-specific. For situations such as posterior free-end implant restorations supporting significant occlusal loads, these movements can negate the effectiveness of the implant restoration over time, placing unfavorable stresses on the remaining dentition.

When natural teeth are present in the same arch with dental implants, an unforeseen long-term complication observed by many has been the opening of contacts between the implant restoration and typically the natural tooth anterior to the implant restoration. With loss of the natural tooth contact mesial to the implant restoration significantly affected by age, condition of the opposing dentition, vitality of the adjacent tooth, and splinting of the anterior natural teeth. Loss of the contact is not gender-specific but appears to be more common in the lower jaw, and the rate increased over time.

Besides functional changes and consequences in occlusion and opening of contacts, it has been observed that subtle growth over time also can change esthetic results once thought to be stable. Discrepancies have become manifest in three visible areas relative to adjacent teeth: the incisal edge length, the gingival margin height, and the facial contour alignment. Extrusion and lingual tipping of anterior maxilla and teeth can simultaneously cause all three discrepancies. Thinning of labial soft tissue over the implant or abutment can be a further consequence accompanying this subtle growth process.

A discrepancy in facial alignment making the anterior implant restoration relatively more labial may or may not be able to be suitably modified or revised, depending not only on the severity of the occurrence but also on such factors as implant axial alignment, available soft-tissue depth, and labial/palatal positioning of the implant in the ridge. A progressive discrepancy between the implant restoration's cervical gingival margin and that of the adjacent natural teeth may be an esthetic complication with no easy resolution.

In view of the above, a need exists for an improved dental implant.

BRIEF DESCRIPTION OF THE FIGURES

FIG. 1a depicts a dental implant partially placed in a patient's alveolus as known in the art.

FIG. 1b depicts the dental implant shown in FIG. 1a placed in the patient's alveolus as known in the art.

FIG. 1c depicts an abutment being coupled with the dental implant shown in FIG. 1a as known in the art.

FIG. 1d depict a tooth analogue being coupled with the abutment shown in FIG. 1c as known in the art.

FIG. 7b depicts a top plan view of the dental implant shown in FIG. 7a.

FIG. 7c depicts a cross-sectional view of the dental implant fixture shown in FIG. 7a.

In the following description, like reference numbers are used to identify like elements. Furthermore, the drawings are intended to illustrate major features of exemplary embodiments in a diagrammatic manner. The drawings are not intended to depict every feature of every implementation nor relative dimensions of the depicted elements, and are not drawn to scale.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

According to one aspect, an implant fixture implantable in an alveolus of a patient's jawbone is presently disclosed. The implant fixture comprises an elongated shaft section, and a head section comprising at least one narrower side surface area, wherein the narrow side surface area provides an area for bone growth therein to compensate for jawbone deterioration adjacent to the implant fixture due to craniofacial growth According to another aspect, an implant fixture implantable in an alveolus of a patient's jawbone is presently disclosed. The implant fixture comprises an elongated shaft section, and a head section, wherein the head section comprises at least one concave area for bone growth therein.

According to another aspect, an implant fixture implantable in an alveolus of a patient's jawbone is presently disclosed. The implant fixture comprises an elongated shaft section with a distal end, and a head section with a proximal end, wherein the head section comprises a first diameter adjacent to the elongated shaft section and a second diameter adjacent to the proximal end, wherein the elongated shaft section comprises a first diameter adjacent to the head section and a second diameter adjacent to the distal end, wherein the second diameter of the head section is less than the first diameter of the elongated shaft section.

Figure 2A:
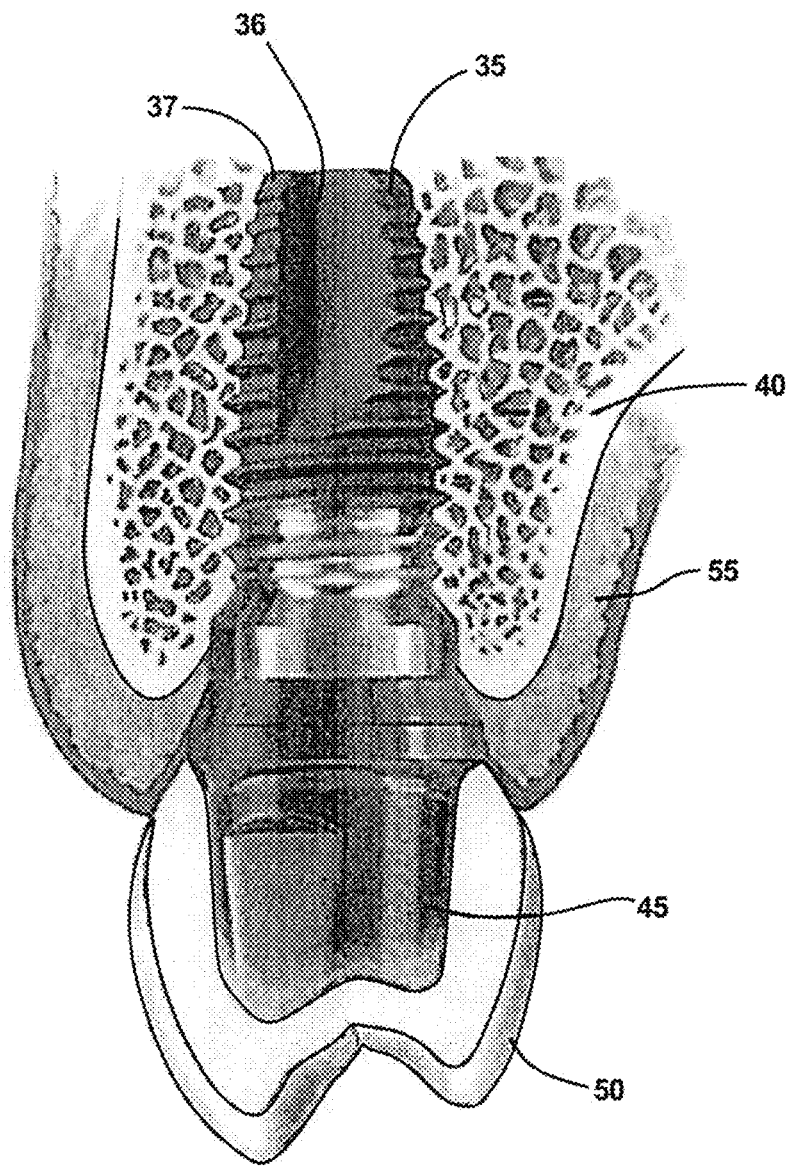
FIG. 2a depicts a dental implant fixture known in the art embedded within an alveolus.

FIG. 2a depicts a dental implant fixture 35 as known in the art embedded within an alveolus formed in a jawbone 40 and coupled with an abutment member 45 and tooth analogue 50. The dental implant fixture 35 comprises a longitudinal groove (i.e. back cut) 36 extending from the narrow distal end 37 towards the abutment member 45. The longitudinal groove 36 provides a greater surface area into which bone growth are formed to prevent the implant fixture 35 from vertical and rotational movements within the jawbone 40.

Figure 2B:
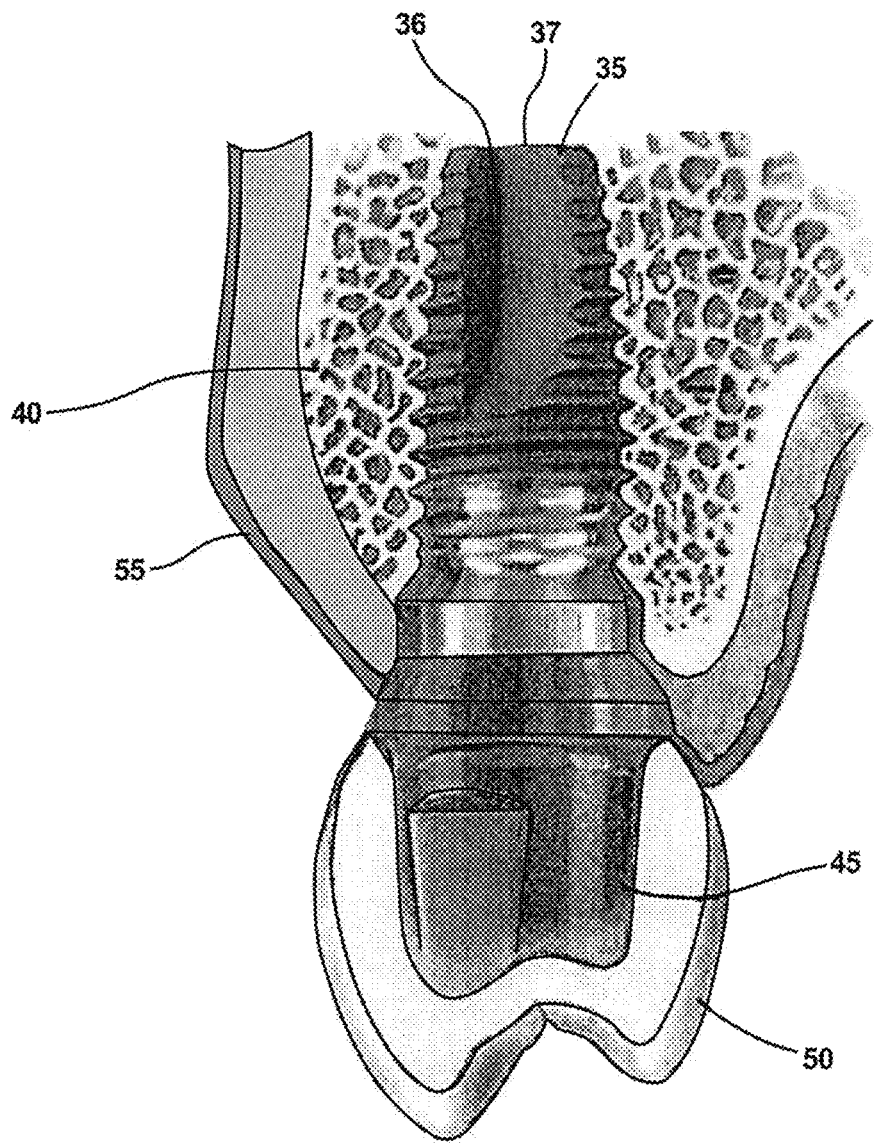
FIG. 2b depicts deterioration of tissue adjacent to the dental fixture shown in FIG. 2a as known in the art.

Due to craniofacial growth, over time, the jawbone 40 and/or soft tissue 55 may at least partially deteriorate adjacent to the dental implant fixture 35 to expose the dental implant fixture 35 and/or the abutment member 45 as shown in FIG. 2b. When this occurs, the dental implant fixture 35 is removed using processes known in the art. The process of removing the dental implant fixture 35 is complex at least in part due to the bone growth within the longitudinal groove 36 which prevent the dental implant fixture 35 from being unscrewed from the jawbone 40.

Figure 3A:
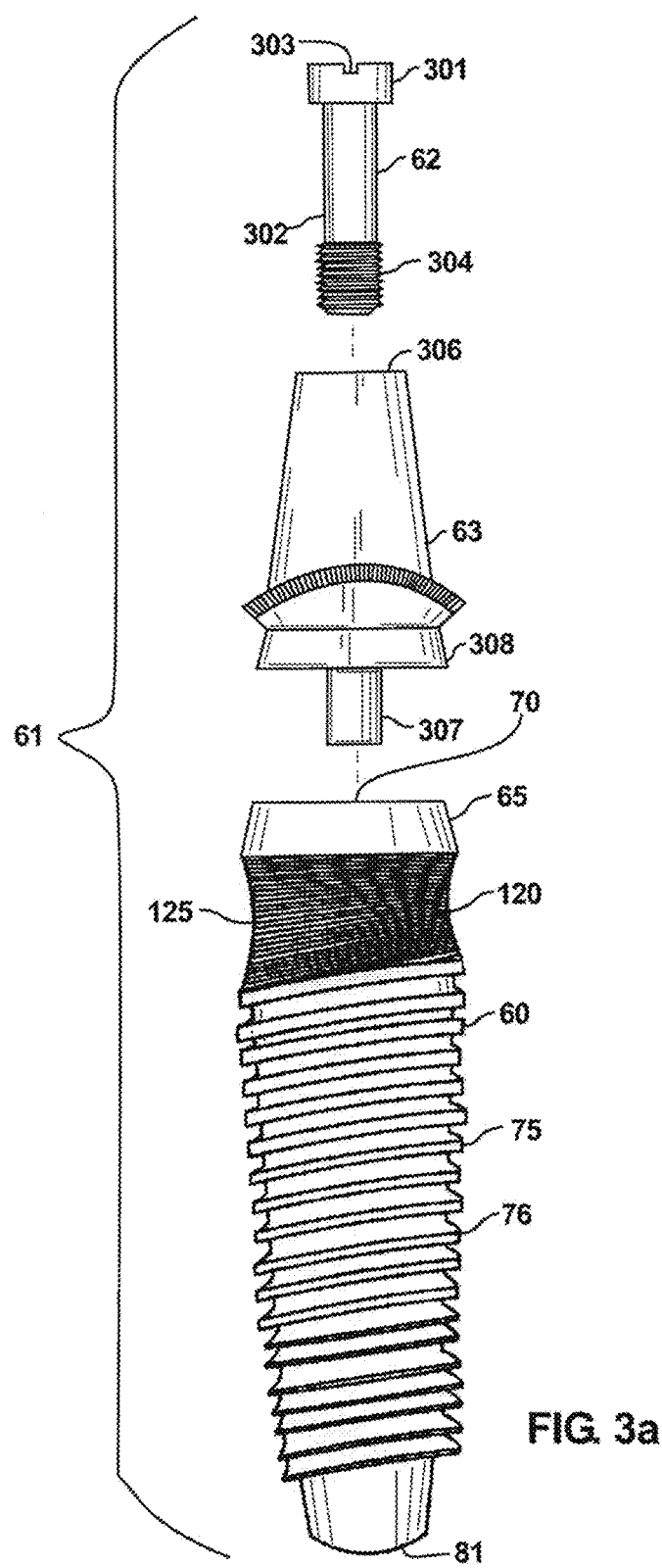
FIG. 3a depicts a dental implant system according to some embodiments of the present disclosure.

Referring to FIG. 3a, a dental implant system 61 is shown according to the present disclosure. In some embodiments, the dental implant system 61 comprises a bolt member 62, an abutment member 63, and a dental implant fixture 60.

In some embodiments, the bolt member 62 comprises a head segment 301 and a shaft segment 302. In some embodiments, the head segment 301 is generally disc shaped with a top notch or cross notch 303 or any other suitable means to accommodate a driving tool, for example, a screwdriver or any other tool for rotating the bolt member 62. In some embodiments, the shaft segment 302 has one end coupled with the head segment 301. In some embodiments, the shaft segment 302 comprises an outer screw threads 304 which are located opposite from the head segment 301 and extend along at least a portion of its length.

Figure 3B:
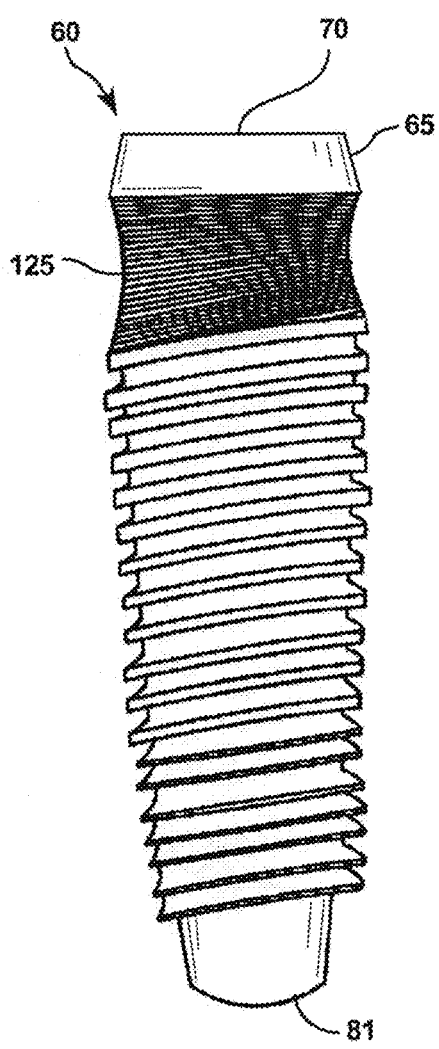
FIG. 3b depicts a dental implant fixture according to some embodiments of the present disclosure.

Referring to FIG. 3b, a dental implant fixture 60 is shown according to the present disclosure. In some embodiments presently disclosed, the dental implant fixture 60 comprises a head section 65 with a proximal end 70. In some embodiments, the fixture 60 comprises an elongated shaft section 75 with a distal end 81. In some embodiments, the head section 65 is integrally coupled with the shaft section 75 to form a one-piece implant fixture 60. This prevents bacteria or other infection growth between the head section and the shaft section of the implant fixture 60. In some embodiments, the elongated shaft section 75 is tapered.

Figure 4:
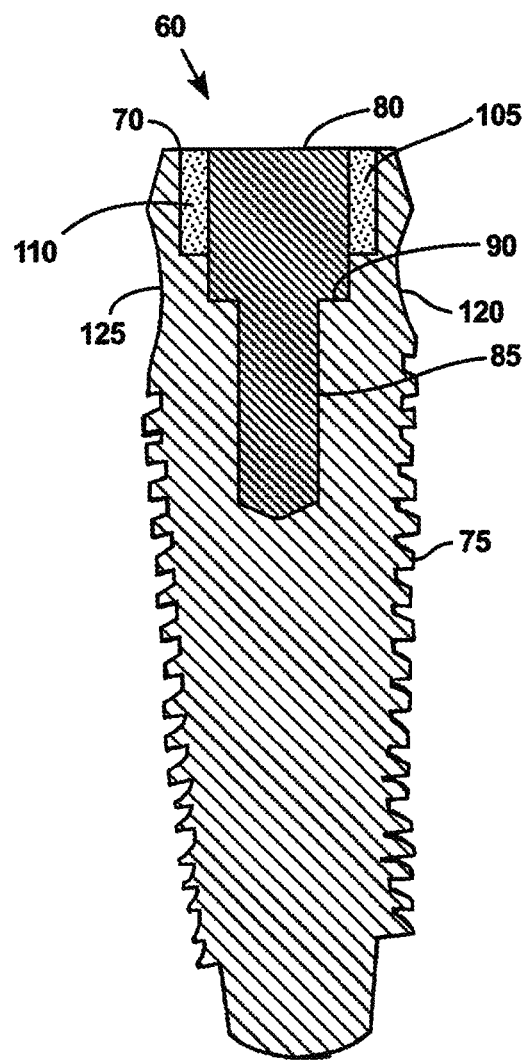
FIG. 4 depicts a cross-sectional view of the dental implant fixture shown in FIG. 3b.

In some embodiments, the implant fixture 60 comprises a stepped interior closed bore 80 extending partially downward from the proximal end 70 into the shaft section 75. In some embodiments, the stepped interior closed bore 80 is off-center. In some embodiments, the interior closed bore 80 comprises inner screw threads 85 along at least a portion of its length and an annular shelf 90 located above the inner screw threads 85 (as shown in FIG. 4). In some embodiment, the inner screw threads 85 are configured to accommodate the outer screw threads 304 of the bolt member 62. In some embodiments, the stepped interior closed bore 80 is configured to accommodate a protruding engagement end 307 (described in more detail below) of the abutment member 63.

Figure 5A:
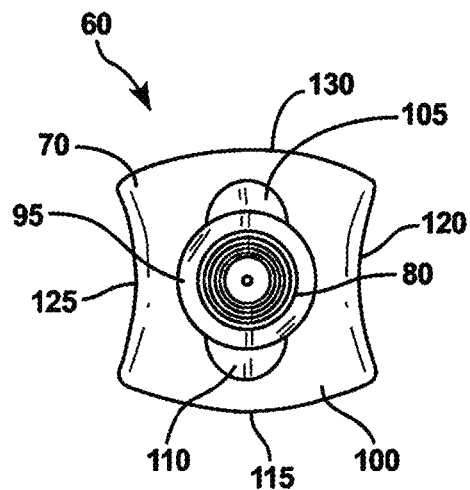
FIG. 5a depicts a top plan view of the dental implant fixture shown in FIG. 3b.

Referring to FIG. 5a, a top plan view of the implant fixture 60 is shown according to some embodiments presently disclosed. In some embodiments, the proximal end 70 has a circular flat surface 95 surrounded by a periphery surface 100 comprising a long-axis and a short axis. In some embodiments, the proximal end 70 further comprises two or more apertures 105, 110 for accommodating small tips of a standard dental tool, for example, implant mount or hand driver for orienting the implant fixture 60. In some embodiments, the head section 65 comprises at least one narrower facial-side surface area 120 and at least one wider interproximal-side surface area 115. The facial-side surface area 120 accommodates the contour of the gingival tissue at the facial-side of the patient's oral cavity, which is located adjacent to the interior surface of the patient's lip, while the interproximal-side surface area 115 accommodates the contour of the gingival tissue at the interproximal-side of the patient's oral cavity which is located adjacent to the patient's other tooth and/or implant. In some embodiments, the facial-side surface area 120 is concaved toward the center of the circular flat surface 95.

In some embodiments, the head section 65 comprises a narrower lingual-side surface area 125 and at least one wider interproximal-side surface area 130. The lingual-side surface area 125 accommodates the contour of the gingival tissue at the lingual-side of the patient's oral cavity which is located adjacent to the patient's tongue or palate, while the interproximal-side surface area 130 accommodates the contour of the gingival tissue at the interproximal-side of the patient's oral cavity which is located adjacent to the patient's other tooth and/or implant. In some embodiments, the lingual-side surface area 125 is concaved toward the center of the circular flat surface 95.

In some embodiments, the facial-side surface area 120 and/or the lingual-side surface area 125 provide an area for bone growth therein to compensate for jawbone deterioration adjacent to the implant fixture 60 due to craniofacial growth. In some embodiments, the facial-side surface area 120 and/or the narrower lingual-side surface area 125 provide an arch shaped area for bone growth therein to compensate for jawbone deterioration adjacent to the implant fixture 60 due to craniofacial growth. In some embodiments, the facial-side surface area 120 and/or the narrower lingual-side surface area 125 provide a flat area (shown in FIG. 5c) for bone growth to compensate for jawbone deterioration adjacent to the implant fixture 60 due to craniofacial growth. In some embodiments, the facial-side surface area 120 and/or the narrower lingual-side surface area 125 provide a concave shaped area for bone growth therein to compensate for jawbone deterioration adjacent to the implant fixture 60 due to craniofacial growth.

Increasing bone volume and/or soft tissue volume adjacent to the facial-side surface area 120 and/or the narrower lingual-side surface area 125 prevents early exposure of the implant fixture 60.

In some embodiments, the facial-side surface area 120 and/or the lingual-side surface area 125 provide a concave shaped area to improve bone formation due to the gap between the existing bone and the facial-side surface area 120 and/or the lingual-side surface area 125. In some embodiments, the facial-side surface area 120 and/or the lingual-side surface area 125 provide a concave shaped area to allow greater bone growth therein. In some embodiments, the facial-side surface area 120 and/or the lingual-side surface area 125 provide a concave shaped area to prevent/minimize pressure between the bone and the head section 65 during and/or immediately after the procedure. Preventing and/or minimizing pressure between the bone and the head section 65 during and/or immediately after the procedure prevent resorption of the bone around the head section 65 and/or allows increased bone formation around the head section 65. In some embodiments, the facial-side surface area 120 and/or the lingual-side surface area 125 provide a concave shaped area to allow bone and/or soft tissue growth therein.

In some embodiments, the dental implant fixture 60 does not comprise the longitudinal groove 36 (shown in FIGS. 2a-b) to prevent bone growth therein so as to allow the dental implant fixture 60 to be removed with less damage to patient's jawbone. In some embodiments, the facial-side surface area 120 and/or the lingual-side surface area 125 provide an area where bone growth can grow therein to prevent the implant fixture 60 from vertical and rotational movements within the patient's jawbone.

In some embodiments, the shaft section 75 comprises an outer screw thread 76 extending along at least a portion of its length. In some embodiments, the outer screw thread 76 is continuous. In some embodiments, the outer screw thread 76 is V-Thread, Square Thread, Buttress Thread, Reverse Buttress Thread or a combination of two or more of these threads. In some embodiments, the shaft section 75 comprises a substantially longitudinal groove or back cut (not shown) extending from the distal end 81 towards the head section 65. The longitudinal groove (not shown) provides a greater surface area into which bone growth is formed to prevent the implant fixture 60 from vertical and rotational movements within the jawbone.

Referring to FIG. 3a, in some embodiments, an abutment member 63 comprises a distal end 306 with a circular opening to accommodate the shaft segment 302 of the bolt member 62. Referring to FIG. 3a, in some embodiments, an abutment member 63 comprises a proximal portion 308 with a protruding engagement end 307 extending therefrom.

Figure 5B:
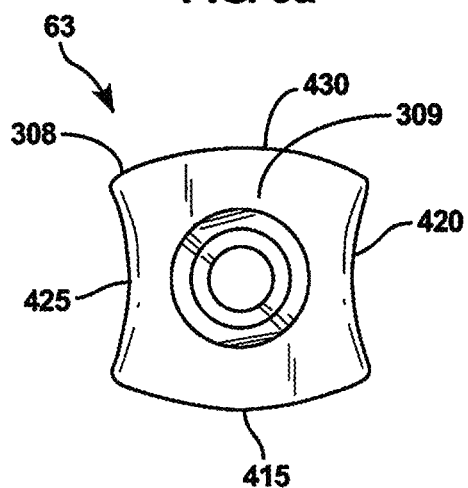
FIG. 5b depicts a bottom plan view of an abutment member according to some embodiments of the present disclosure.
Figure 5C:
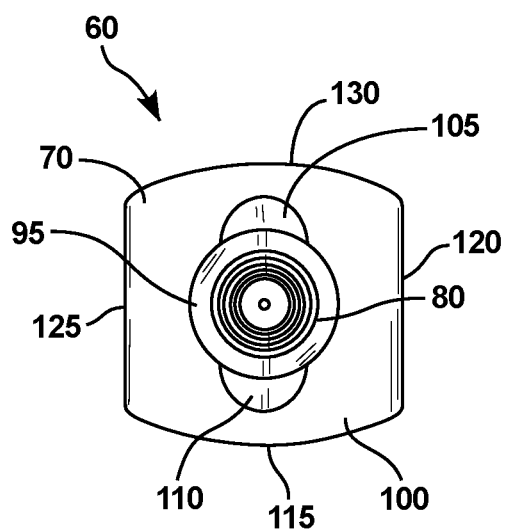
FIG. 5c depicts a top plan view of a dental implant fixture according to some embodiments of the present disclosure.

Referring to FIG. 5b, a bottom plan view of the abutment member 63 is shown according to some embodiments presently disclosed. According to some embodiments, the proximal portion 308 comprises a surface 309. In some embodiments, the surface 309 comprises a long-axis and a short axis. In some embodiments, the proximal portion 308 comprises at least one narrower facial-side surface area 420 and at least one wider interproximal-side surface area 415. In some embodiments, the facial-side surface area 420 is substantially similar to the facial-side surface area 120. In some embodiments, the interproximal-side surface area 415 is substantially similar to the interproximal-side surface area 115. In some embodiments, the facial-side surface area 420 is concaved toward the center of the abutment member 63.

In some embodiments, the proximal portion 308 comprises a narrower lingual-side surface area 425 and at least one wider interproximal-side surface area 430. In some embodiments, the lingual-side surface area 425 is substantially similar to the lingual-side surface area 125. In some embodiments, the interproximal-side surface area 430 is substantially similar to the interproximal-side surface area 130. In some embodiments, the lingual-side surface area 425 is concaved toward the center of the abutment member 63.

Figure 3C:
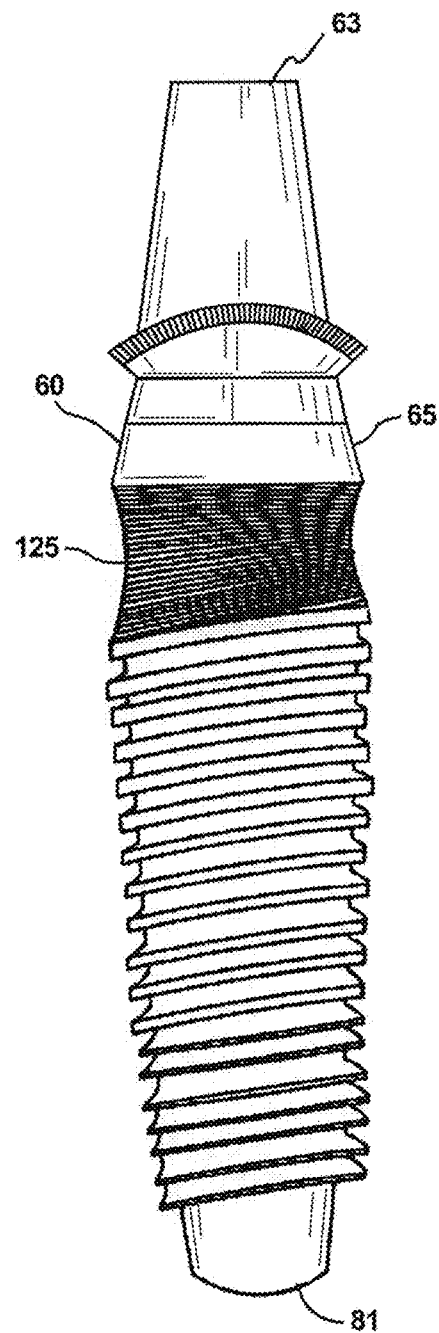
FIG. 3c depicts a dental implant fixture according to some embodiments of the present disclosure.

In some embodiment, an abutment member 63 is configured to couple with the head section 65 as shown in FIG. 3c. In some embodiment, an abutment member 63 is configured to couple with the head section 65 so as to align the facial-side surface area 420 with the facial-side surface area 120. In some embodiment, an abutment member 63 is configured to couple with the head section 65 so as to align the interproximal-side surface area 415 with the interproximal-side surface area 115. In some embodiment, an abutment member 63 is configured to couple with the head section 65 so as to align the lingual-side surface area 425 with the lingual-side surface area 125. In some embodiment, an abutment member 63 is configured to couple with the head section 65 so as to align the interproximal-side surface area 430 with the interproximal-side surface area 130.

In some embodiments, the facial-side surface area 420 and/or the lingual-side surface area 425 provide an area for bone growth therein to compensate for jawbone deterioration adjacent to the abutment member 63 due to craniofacial growth. In some embodiments, the facial-side surface area 420 and/or the narrower lingual-side surface area 425 provide an arch shaped area for bone growth therein to compensate for jawbone deterioration adjacent to abutment member 63 due to craniofacial growth. In some embodiments, the facial-side surface area 420 and/or the narrower lingual-side surface area 425 provide a flat area for bone growth to compensate for jawbone deterioration adjacent to abutment member 63 due to craniofacial growth. In some embodiments, the facial-side surface area 420 and/or the narrower lingual-side surface area 425 provide a concave shaped area for bone growth therein to compensate for jawbone deterioration adjacent to abutment member 63 due to craniofacial growth. Increasing bone volume and/or soft tissue volume adjacent to the facial-side surface area 420 and/or the narrower lingual-side surface area 425 prevents early exposure of the abutment member 63.

In some embodiments, the facial-side surface area 420 and/or the lingual-side surface area 425 provide a concave shaped area to improve bone formation due to the gap between the existing bone and the facial-side surface area 420 and/or the lingual-side surface area 425. In some embodiments, the facial-side surface area 420 and/or the lingual-side surface area 425 provide a concave shaped area to allow greater bone growth therein. In some embodiments, the facial-side surface area 420 and/or the lingual-side surface area 425 provide a concave shaped area to prevent/minimize pressure between the bone and the abutment member 63 during and/or immediately after the procedure. Preventing and/or minimizing pressure between the bone and the abutment member 63 during and/or immediately after the procedure prevent resorption of the bone around the abutment member 63 and/or allows increased bone formation around the abutment member 63. In some embodiments, the facial-side surface area 420 and/or the lingual-side surface area 425 provide a concave shaped area to allow bone and/or soft tissue growth therein.

Figure 6:
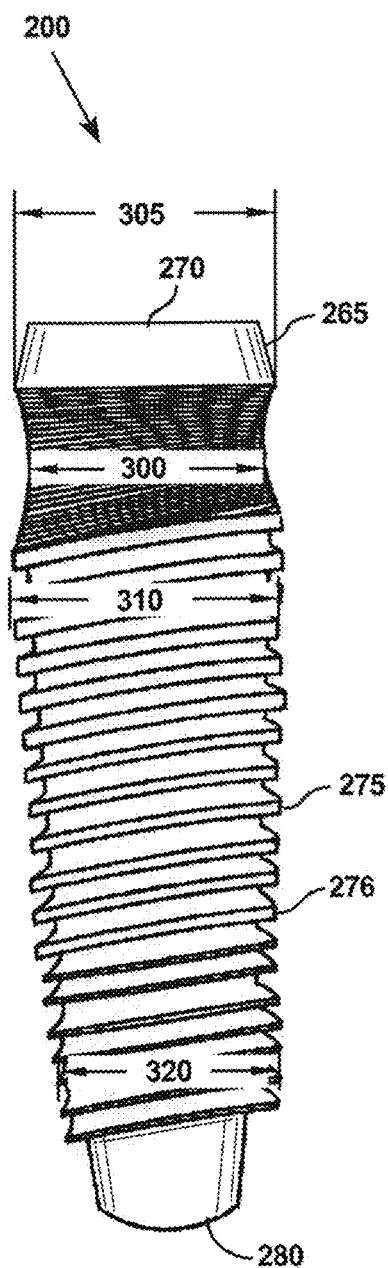
FIG. 6 depicts another dental implant fixture according to some embodiments of the present disclosure.

Referring to FIG. 6, a dental implant fixture 200 is shown according to the present disclosure. In some embodiments presently disclosed, the dental implant fixture 200 comprises a head section 265 with a proximal end 270. In some embodiments, the fixture 200 comprises an elongated shaft section 275 with a distal end 280. In some embodiments, the head section 265 is integrally coupled with the shaft section 275 to form a one-piece implant fixture 200. This prevents bacteria or other infection growth between the head section and the shaft section of the implant fixture 200. In some embodiments, the elongated shaft section 275 is tapered.

Referring to FIG. 6, in some embodiments, the head section 265 is substantially circular comprising a first head section diameter 300 adjacent to the shaft section 275 and comprising a second head section diameter 305 adjacent to the proximal end 270. In some embodiments, the shaft section 275 is substantially circular comprising a first shaft diameter 310 adjacent to the head section 265 and comprising a second shaft diameter 320 adjacent to the distal end 280.

In some embodiments, the first head section diameter 300 is less than the first shaft diameter 310. In some embodiments, the second head section diameter 305 is less than the first shaft diameter 310. In some embodiments, the first head section diameter 300 and the second head section diameter 305 are less than the first shaft diameter 310. In some embodiments, the first head section diameter 300 and the second head section diameter 305 are substantially equal to the first shaft diameter 310. In some embodiments, the second head section diameter 305 is substantially equal to the first shaft diameter 310. In some embodiments, the first shaft diameter 310 is substantially equal to the second shaft diameter 320. In some embodiments, the second shaft diameter 320 is less than the first shaft diameter 310.

In some embodiments, the head section 265 provides an area for bone growth therein to compensate for jawbone deterioration adjacent to the implant fixture 200 due to craniofacial growth. In some embodiments, the head section 265 provides an arch shaped area for bone growth therein to compensate for jawbone deterioration adjacent to the implant fixture 200 due to craniofacial growth. In some embodiments, the head section 265 provides a concave shaped area to allow bone growth therein to compensate for jawbone deterioration adjacent to the implant fixture 200 due to craniofacial growth. Increasing bone volume and/or soft tissue volume adjacent to the head section 265 prevents early exposure of the dental implant fixture 200.

In some embodiments, the head section 265 provides a concave shaped area to improve bone formation due to the gap between the existing bone and the concave shaped area. In some embodiments, the head section 265 provides a concave shaped area to allow greater bone growth therein. In some embodiments, the head section 265 provides a concave shaped area to prevent/minimize pressure between the bone and the head section 265 during and/or immediately after the procedure. Preventing and/or minimizing pressure between the bone and the head section 265 during and/or immediately after the procedure prevent resorption of the bone around the head section 265 and/or allows increased bone formation around the head section 265. In some embodiments, the head section 265 provides a concave shaped area to allow bone and/or soft tissue growth therein.

In some embodiments, the shaft section 275 comprises an outer screw thread 276 extending along at least a portion of its length. In some embodiments, the outer screw thread 276 is continuous. In some embodiments, the outer screw thread 276 is V-Thread, Square Thread, Buttress Thread, Reverse Buttress Thread or a combination of two or more of these threads. In some embodiments, the shaft section 275 comprises a substantially longitudinal groove (not shown) extending from the distal end 280 towards the head section 265. The longitudinal groove (not shown) provides a greater surface area into which bone growth is formed to prevent the implant fixture 200 from vertical and rotational movements within the jawbone.

Figure 7B:
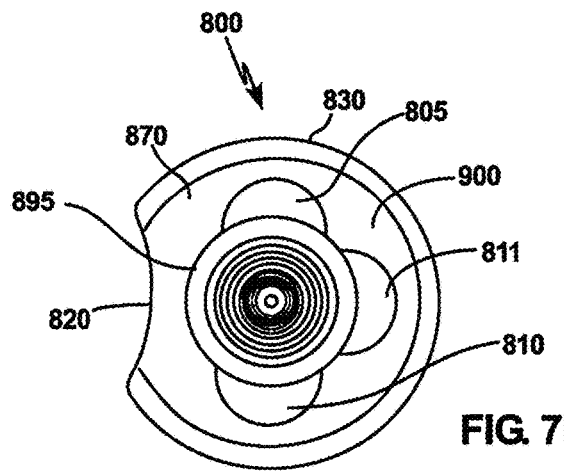
Figure 7A:
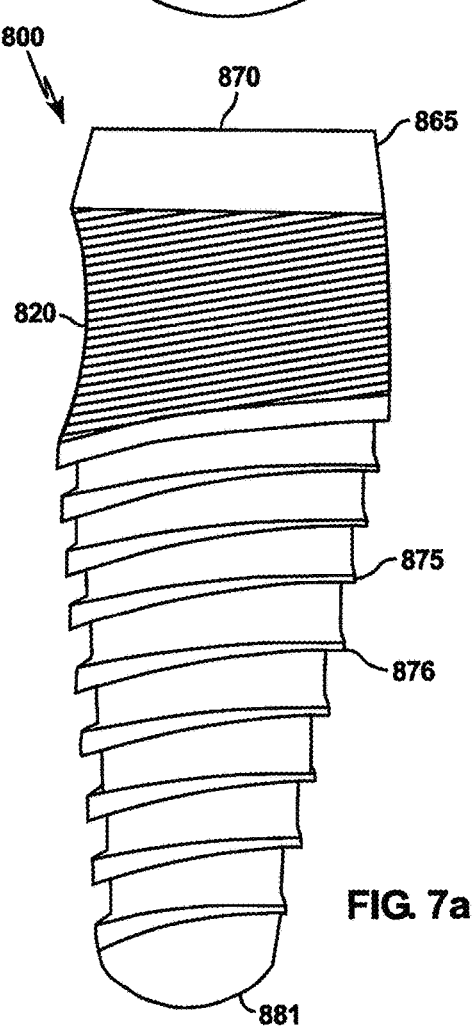
FIG. 7a depicts the dental implant fixture according to some embodiments of the present disclosure.
Figure 7C:
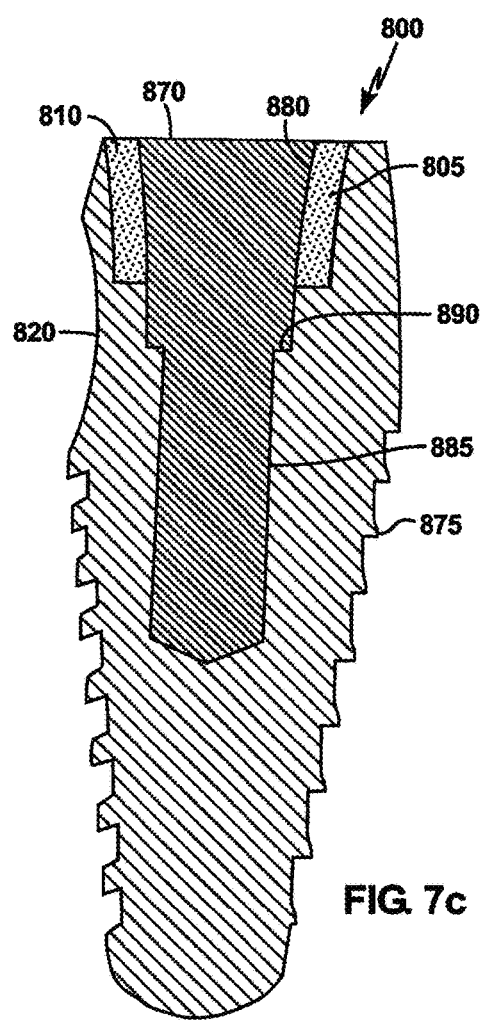

Referring to FIGS. 7a-c, a dental implant fixture 800 is shown according to the present disclosure. In some embodiments presently disclosed, the dental implant fixture 800 comprises a head section 865 with a proximal end 870. In some embodiments, the fixture 800 comprises an elongated shaft section 875 with a distal end 881. In some embodiments, the head section 865 is integrally coupled with the shaft section 875 to form a one-piece implant fixture 800. This prevents bacteria or other infection growth between the head section and the shaft section of the implant fixture 800. In some embodiments, the elongated shaft section 875 is tapered.

In some embodiments, the implant fixture 800 comprises a stepped interior closed bore 880 extending partially downward from the proximal end 870 into the shaft section 875 as shown in FIG. 7c. In some embodiments, the stepped interior closed bore 880 is off-center. In some embodiments, the interior closed bore 880 comprises inner screw threads 885 along at least a portion of its length and an annular shelf 890 located above the inner screw threads 885 (as shown in FIG. 7c). In some embodiment, the inner screw threads 885 are configured to accommodate the outer screw threads 304 of the bolt member 62. In some embodiments, the stepped interior closed bore 880 is configured to accommodate a protruding engagement end 307 (described in more detail above) of the abutment member 63.

Referring to FIG. 7b, a top plan view of the implant fixture 800 is shown according to some embodiments presently disclosed. In some embodiments, the proximal end 870 has a circular flat surface 895 surrounded by a periphery surface 900 comprising a long-axis and a short axis. In some embodiments, the proximal end 870 further comprises two or more apertures 805, 810, 811 for accommodating small tips of a standard dental tool, for example, implant mount or hand driver for orienting the implant fixture 800. In some embodiments, the head section 865 comprises at least one narrower facial-side surface area 820 and at least one wider surface area 830. The facial-side surface area 820 accommodates the contour of the gingival tissue at the facial-side of the patient's oral cavity, which is located adjacent to the interior surface of the patient's lip, while the surface area 830 accommodates the contour of the gingival tissue at the interproximal-side of the patient's oral cavity which is located adjacent to the patient's other tooth and/or implant.

In some embodiments, the surface area 830 accommodates the contour of the gingival tissue at the lingual-side of the patient's oral cavity which is located adjacent to the patient's tongue or palate. In some embodiments, the surface area 830 accommodates the contour of the gingival tissue at the lingual-side of the patient's oral cavity which is located adjacent to the patient's tongue or palate and accommodates the contour of the gingival tissue at the interproximal-side of the patient's oral cavity which is located adjacent to the patient's other tooth and/or implant(s). In some embodiments, the facial-side surface area 820 is concaved toward the center of the implant fixture 800.

Figure 7D:
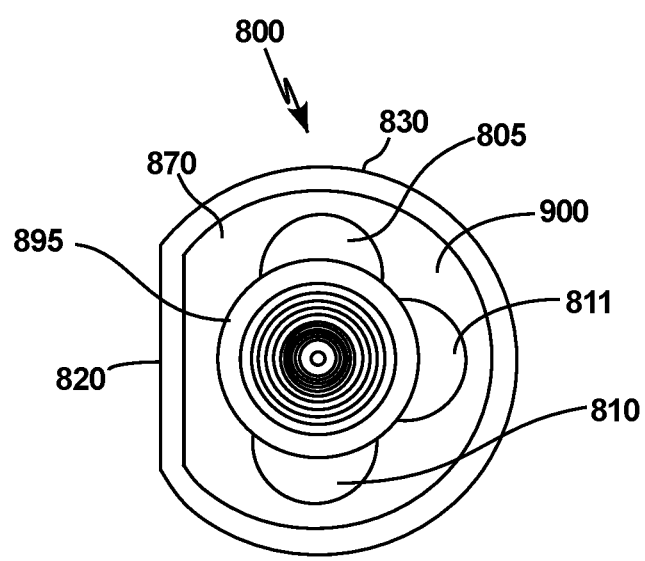
FIG. 7d depicts a top plan view of a dental implant fixture according to some embodiments of the present disclosure.

In some embodiments, the facial-side surface area 820 provides an area for bone growth therein to compensate for jawbone deterioration adjacent to the implant fixture 800 due to craniofacial growth. In some embodiments, the facial-side surface area 820 provides an arch shaped area for bone growth therein to compensate for jawbone deterioration adjacent to the implant fixture 800 due to craniofacial growth. In some embodiments, the facial-side surface area 820 provides a flat area (shown in FIG. 7d) for bone growth to compensate for jawbone deterioration adjacent to the implant fixture 800 due to craniofacial growth. In some embodiments, the facial-side surface area 820 provides a concave shaped area for bone growth therein to compensate for jawbone deterioration adjacent to the implant fixture 800 due to craniofacial growth. Increasing bone volume and/or soft tissue volume adjacent to the facial-side surface area 820 prevents early exposure of the implant fixture 800.

In some embodiments, the facial-side surface area 820 provides a concave shaped area to improve bone formation due to the gap between the existing bone and the facial-side surface area 820. In some embodiments, the facial-side surface area 820 provides a concave shaped area to allow greater bone growth therein. In some embodiments, the facial-side surface area 820 provides a concave shaped area to prevent/minimize pressure between the bone and the implant fixture 800 during and/or immediately after the procedure. Preventing and/or minimizing pressure between the bone and the implant fixture 800 during and/or immediately after the procedure prevent resorption of the bone around the implant fixture 800 and/or allows increased bone formation around the implant fixture 800. In some embodiments, the facial-side surface area 820 provides a concave shaped area to allow bone and/or soft tissue growth therein.

In some embodiments, the dental implant fixture 800 does not comprise the longitudinal groove 36 (shown in FIGS. 2a-b) to prevent bone growth therein so as to allow the dental implant fixture 800 to be removed with less damage to patient's jawbone. In some embodiments, the facial-side surface area 820 provides an area where bone growth can grow therein to prevent the implant fixture 800 from vertical and rotational movements within the patient's jawbone.

In some embodiments, the shaft section 875 comprises an outer screw thread 876 (shown in FIG. 7a) extending along at least a portion of its length. In some embodiments, the outer screw thread 876 is continuous. In some embodiments, the outer screw thread 876 is V-Thread, Square Thread, Buttress Thread, Reverse Buttress Thread or a combination of two or more of these threads. In some embodiments, the shaft section 875 comprises a substantially longitudinal groove or back cut (not shown) extending from the distal end 881 towards the head section 865. The longitudinal groove (not shown) provides a greater surface area into which bone growth is formed to prevent the implant fixture 800 from vertical and rotational movements within the jawbone.

While several illustrative embodiments of the invention have been shown and described, numerous variations and alternative embodiments will occur to those skilled in the art. Such variations and alternative embodiments are contemplated, and can be made without departing from the scope of the invention as defined in the appended claims.

As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The foregoing detailed description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . ."

What is claimed is:

1. An implant fixture adapted for implanting into an alveolus of a jawbone of a patient, the jawbone including a facial side and a lingual side, the implant fixture comprising:
   a. a head section integrally coupled with a shaft section to form a one-piece implant;
   b. the head section including a concave facial sidewall having a concavity extending radially inward into the head section;
   c. the head section including a concave lingual sidewall having a concavity extending radially inward into the head section; and
   d. the concavity of the lingual sidewall taller than the concavity of the facial sidewall;
   e. wherein the concave facial sidewall provides a concave shape area for bone growth therein to compensate for jawbone deterioration adjacent to the implant fixture due to craniofacial growth and promotes bone volume and/or soft tissue volume adjacent the facial side surface area and the concave lingual sidewall provides a concave shape area for bone growth therein to compensate for jawbone deterioration adjacent to the implant fixture due to craniofacial growth and promotes bone volume and/or soft tissue volume adjacent the lingual side surface area.

2. An implant fixture adapted for implanting into an alveolus of a jawbone of a patient, the jawbone including a facial side and a lingual side, the implant fixture comprising:
   a. a head section integrally coupled with a shaft section to form a one-piece implant;
   b. the head section including a concave facial sidewall having a concavity extending radially inward into the head section; and
   c. the head section including a concave lingual sidewall having a concavity extending radially inward into the head section;
   d. wherein the concave facial sidewall provides a concave shape area for bone growth therein to compensate for jawbone deterioration adjacent to the implant fixture due to craniofacial growth and promotes bone volume and/or soft tissue volume adjacent the facial side surface area and the concave lingual sidewall provides a concave shape area for bone growth therein to compensate for jawbone deterioration adjacent to the implant fixture due to craniofacial growth and promotes bone volume and/or soft tissue volume adjacent the lingual side surface area.

3. The implant fixture in accordance with claim 2 comprising: said shaft section tapering from the location where the shaft section is integrally coupled with the head section to a distal end.

4. The implant fixture in accordance with claim 3 comprising: the shaft section having an outer surface with screw threads continuously extending from the location where the shaft section is integrally coupled with the head section to a location above and spaced apart from the distal end of the shaft section.

* * * * *